United States Patent [19]

Maurer et al.

[11] 4,321,408
[45] Mar. 23, 1982

[54] PREPARATION OF 1,3-DIBROMO-2,2-DIMETHYL-PROPANE-1,3-DICARBOXYLIC ACID DERIVATIVES

[75] Inventors: Fritz Maurer, Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 153,297

[22] Filed: May 27, 1980

[30] Foreign Application Priority Data

Jun. 12, 1979 [DE] Fed. Rep. of Germany ....... 2923775

[51] Int. Cl.$^3$ .................... C07C 67/307; C07C 51/58; C07C 51/60
[52] U.S. Cl. ............................. 560/192; 260/544 R; 260/544 Y
[58] Field of Search ..................... 560/192; 260/544 Y, 260/544 K

[56] References Cited

PUBLICATIONS

Perkin et al., J. Chem. Soc. 79, pp. 753–755 (1901).
Sweet et al., J. Org. Chem. 21 pp. 1426–1429 (1926).
Weygand, *Preparative Organic Chemistry*, pp. 243–247 and 172–180 (1972).
Chemical Abstracts, vol. 43, 1325b, (1949).
Houben-Weyl, vol. 5/4, pp. 202–203 (1960).

*Primary Examiner*—Natalie Trousof
*Assistant Examiner*—Vera C. Clarke
*Attorney, Agent, or Firm*—Sprung, Felfe, Horn, Lynch & Kramer

[57] ABSTRACT

In the preparation of a 1,3-dibromo-2,2-dimethyl-propane-1,3-dicarboxylic acid derivative of the formula

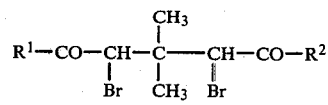

in which $R^1$ and $R^2$ each independently is chlorine or alkoxy, by reacting a 2,2-dimethyl-propane-1,3-dicarboxylic acid derivative of the formula

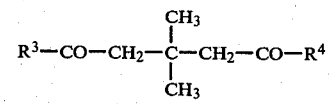

in which
$R^3$ is hydroxy or alkoxy and
$R^4$ is hydroxy, or
$R^3$ and $R^4$ together are an anhydride oxygen atom,
with an acid halide, then reacting the product with bromine at a temperature between 0° and 150° C. to form a 1,3-dibromo-2,2-dimethyl-propane-1,3-dicarboxylic acid chloride and optionally reacting such acid chloride with an alkanol, the improvement which comprises employing an acid chloride as the acid halide, e.g. phosphorus pentachloride, phosphorus oxychloride, phosphorus trichloride, thionyl chloride or phosgene. Compounds of the formula

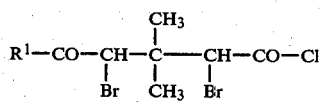

are new. The products are intermediates for making insecticides.

7 Claims, No Drawings

PREPARATION OF 1,3-DIBROMO-2,2-DIMETHYL-PROPANE-1,3-DICARBOXYLIC ACID DERIVATIVES

The invention relates to an unobvious process for the preparation of certain 1,3-dibromo-2,2-dimethyl-propane-1,3-dicarboxylic acid derivatives, some of which are known, and to 1,3-dibromo-2,2-dimethyl-propane-1,3-dicarboxylic acid dichloride and chloride esters as new intermediate products in this process.

It is already known that 1,3-dibromo-2,2-dimethyl-propane-1,3-dicarboxylic acid diethyl ester is obtained when 2,2-dimethyl-propane-1,3-dicarboxylic acid anhydride ($\beta,\beta$-dimethyl-glutaric anhydride) is reacted with phosphorus pentabromide and bromine and the halogenation product is reacted with ethanol (see J. Chem. Soc. (London) 79 (1901), 754).

The use of phosphorus pentabromide, which is expensive and not very stable, evidently arises from the belief that the reaction with bromine can lead selectively to the desired 1,3-dibromo-2,2-dimethyl-propane-dicarboxylic acid derivative only in the presence of an acid bromide.

Because of the significance of 1,3-dibromo-2,2-dimethyl-propane-1,3-dicarboxylic acid derivatives as intermediate products for pyrethroids, there was thus interest in a process by which these compounds can be prepared in good yield and high purity with acceptable technical effort.

The present invention now provides:

(1) a process for the preparation of a 1,3-dibromo-2,2-dimethyl-propane-1,3-dicarboxylic acid derivative of the general formula

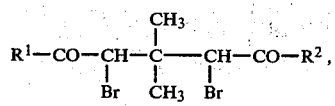

in which
R$^1$ and R$^2$ are identical or different and
each represents chlorine or alkoxy,
in which a 2,2-dimethyl-propane-1,3-dicarboxylic acid derivative of the general formula

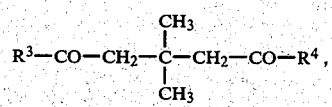

in which
R$^3$ represents hydroxyl or alkoxy and
R$^4$ represents hydroxyl or
R$^3$ and R$^4$ together represent an anhydride-oxygen atom, is first reacted with an acid halide, if appropriate in the presence of a catalyst, and the product is then reacted with bromine at a temperature between 0° and 150° C., and the 1,3-dibromo-2,2-dimethyl-propane-1,3-dicarboxylic acid dichloride or chloride ester, formed in this manner, of the general formula

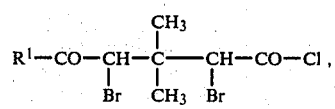

in which R$^1$ represents chlorine or alkoxy, is optionally esterified by reaction with an alcohol by customary methods, characterized in that an acid chloride is employed as the acid halide; and (2) as new compounds, the 1,3-dibromo-2,2-dimethyl-propane-1,3-dicarboxylic acid dichloride and chloride esters of the general formula

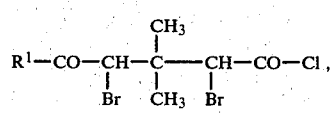

in which R$^1$ represents chlorine or alkoxy.

It is surprising that 1,3-dibromo-2,2-dimethyl-propane-1,3-dicarboxylic acid derivatives of the formulae (I) and (I a) are obtained with very good yields and in high purity by the present process.

A substantial advantage of the present process is that acid chlorides can be used instead of phosphorus pentabromide.

If, for example, 3,3-dimethyl-propane-1,3-dicarboxylic acid is used as the starting compound, phosphorus pentachloride and bromine are used as the halogenating agents and methanol is used as the esterifying agent, the reactions of these compounds in the process according to the invention can be outlined by the following equation:

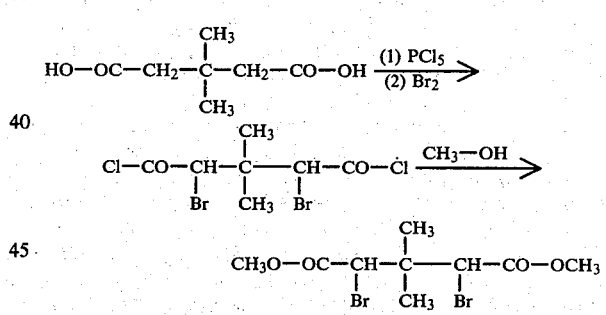

Formula (I a) provides a definition of the new 1,3-dibromo-2,2-dimethyl-propane-1,3-dicarboxylic acid derivatives. Preferably, in this formula, R$^1$ represents chlorine or C$_1$–C$_4$-alkoxy, especially methoxy and ethoxy.

Examples of the new compounds of the formula (I a) which may be mentioned are: 1,3-dibromo-2,2-dimethyl-propane-1,3-dicarboxylic acid dichloride, 1,3-dibromo-2,2-dimethyl-propane-1,3-dicarboxylic acid chloride methyl ester and 1,3-dibromo-2,2-dimethyl-propane-1,3-dicarboxylic acid chloride ethyl ester.

Formula (II) provides a definition of the 2,2-dimethyl-propane-1,3-dicarboxylic acid derivatives to be employed as starting substances. Preferably, in this formula, R$^3$ represents hydroxy or C$_1$–C$_4$-alkoxy, especially methoxy, and
R$^4$ represents hydroxy, or
R$^3$ and R$^4$ together represent an anhydride-oxygen atom.

Examples of the starting compounds of the formula (II) which may be mentioned are: 2,2-dimethyl-propane-1,3-dicarboxylic acid, 2,2-dimethyl-propane-1,3-dicarboxylic acid anhydride, and 2,2-dimethyl-propane-1,3-dicarboxylic acid monomethyl ester, monoethyl ester, mono-n-propyl ester, mono-iso-propyl ester, mono-n-butyl ester, mono-iso-butyl ester, mono-sec.-butyl ester and mono-tert.-butyl ester.

2,2-Dimethyl-propane-1,3-dicarboxylic acid derivatives of the formula (II) are known (see J. Org. Chem. 15 (1950), 850 and 855).

Examples which may be mentioned of acid chlorides which can be employed in the process according to the invention are phosphorus pentachloride, phosphorus oxychloride, phosphorus trichloride, thionyl chloride and phosgene. Phosphorus pentachloride and thionyl chloride are preferably used. Of course, more than one acid chloride may be employed in the reaction.

If appropriate, the process according to the invention is carried out using a catalyst. Possible catalysts are compounds which are usually employed as catalysts for the preparation of carboxylic acid chlorides. These compounds include, as preferences, tertiary and heterocyclic amines, for example triethylamine, N,N-dimethyl-aniline and pyridine; ammonium salts, for example tetraethylammonium chloride; carboxylic acid amides, for example dimethylformamide, dimethylacetamido or N-methyl-pyrrolidone; and phosphorus compounds, for example triphenylphosphine, triphenylphosphine oxide or hexamethyl-phosphoric acid triamide.

In a preferred variant (a) of process (1) according to the invention, 2,2-dimethyl-propane-1,3-dicarboxylic acid anhydride, ($\beta,\beta$-dimethyl-glutaric anhydride) is heated to a temperature of between 80° and 130° C. with about an equimolar amount (0.9 to 1.1 mol equivalents) of phosphorus pentachloride, and, after about 30 minutes at the above temperature, about the stoichiometric amount of bromine (1.9 to 2.2 mols of bromine per mole of anhydride) is added to the mixture.

In a second preferred variant (b) of process (1), a 2,2-dimethyl-propane-1,3-dicarboxylic acid mono-ester ($\beta,\beta$-dimethyl-glutaric acid mono-ester) is warmed to a temperature of between 40° and 90° C. with about 1.2 to 3 mol equivalents of thionyl chloride, if appropriate in the presence of one of the catalysts indicated above, and, after about one hour, about the stoichiometric amount of bromine (1.9 to 2.2 mols of bromine per mol of mono-ester) is added to the mixture at a temperature of between 70° and 90° C.

In a third preferred variant (c) of process (1), 2,2-dimethyl-propane-1,3-dicarboxylic acid ($\beta,\beta$-dimethyl-glutaric acid) is warmed to a temperature of between 40° and 90° C. with about 1.2 to 3 mol equivalents of thionyl chloride, if appropriate in the presence of one of the catalysts indicated above, and, after about 30 minutes at the above temperature, 1 to 1.3 mol equivalents of phosphorus pentachloride are added, about the stoichiometric amount of bromine (1.9 to 2.2 mols of bromine per mol of acid) is then added at a temperature of between 80° and 130° C. and the mixture is stirred at this temperature for 15 to 20 hours.

In a fourth preferred variant (d) of process (1), 2,2-dimethyl-propane-1,3-dicarboxylic acid ($\beta,\beta$-dimethyl-glutaric acid) is reacted with 1.9 to 2.2 mol equivalents of phosphorus pentachloride at a temperature between 10° and 50° C., about the stoichiometric amount of bromine (1.9 to 2.2 mols of bromine per mole of acid) is added to the reaction mixture at a temperature of between 80° and 130° C. and the mixture is stirred at this temperature for 15 to 20 hours.

The 1,3-dibromo-2,2-dimethyl-propane-dicarboxylic acid dichloride and chloride esters of the formula (I a) obtained by process variants (a) to (d) can be purified by distillation. However, the acid chlorides (I a) can also be esterified by customary methods by reaction with preferably $C_1$–$C_4$-alcohols at temperatures between 10° and 80° C. without intermediate isolation, if appropriate after distilling off excess halogenating agent.

For purification and isolation of the esters of the formula (I), the mixture is diluted with water and extracted with a water-immiscible solvent, for example ether or toluene. The organic extracts are washed until neutral, dried and concentrated. The products, which remain in the residue, can be purified by vacuum distillation. The boiling point is used for their characterization.

The 1,3-dibromo-2,2-dimethyl-propane-1,3-dicarboxylic acid esters of the formula (I) to be prepared by the process according to the invention can be used for the preparation of 3,3-dimethyl-cyclopropane-1,2-dicarboxylic acid esters (caronic acid esters). For this, esters of the formula (I) are reacted with about 1.5–2 mole equivalents of zinc, if appropriate in the presence of a diluent, for example dimethylformamide, at a temperature between 20° and 200° C., preferably between 80° and 150° C.

For working up, the mixture is diluted with a water-immiscible solvent, for example toluene, and filtered. The filtrate is washed with dilute hydrochloric acid and then with water, dried and concentrated. The product can be purified by vacuum distillation.

3,3-Dimethyl-cyclopropane-1,2-dicarboxylic acid derivatives can be used as intermediate products for the preparation of insecticidally and acaricidally active pyrethroids (see Pestic. Sci. 7 (1976), 492–498; and Tetrahedron Lett. 1978, 1847–1850).

PREPARATIVE EXAMPLES

Example 1

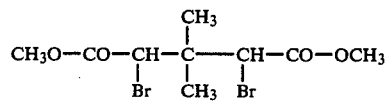

A mixture of 28.4 g (0.2 mol) of $\beta,\beta$-dimethyl-glutaric anhydride and 41.6 g (0.2 mol) of phosphorus pentachloride was heated to 115°–120° C. for half an hour. 64 g (0.4 mol) of bromine were then added dropwise at this temperature. Decoloration occurred immediately. The reaction mixture was cooled to 20° C. 300 ml of methanol were added dropwise at this temperature. After subsequent reaction of the mixture at 20° C. for 12 hours, it was poured into 600 ml of water. The mixture was extracted twice with 200 ml of ether each time. The combined ether extracts were washed with 200 ml of 2% strength sodium carbonate solution, dried over sodium sulphate and evaporated. The residue was distilled. 55 g (79% of theory) of 1,3-dibromo-2,2-dimethyl-propane-1,3-dicarboxylic acid dimethyl ester were obtained in the form of a colorless oil of boiling point 105°–108° C./1 mm Hg.

Example 2

1st stage:

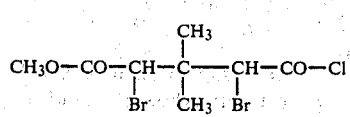

87 g (0.5 mol) of β,β-dimethyl-glutaric acid monoethyl ester (for the preparation, see S. F. Birch et al., J. Chem. Soc. (London) 1952, 1364) were added dropwise to 150 ml of thionyl chloride and the mixture was then boiled under reflux for 1 hour. 170 g of bromine were then added dropwise in the course of about 3 hours, while boiling the mixture further, and, when the addition had ended, the mixture was subsequently boiled for a further 1 hour. The reaction mixture was freed from excess thionyl chloride at about 50° C. in vacuo and was then distilled in vacuo. 145 g (83% of theory) of 1,3-dibromo-2,2-dimethyl-propane-1,3-dicarboxylic acid methyl ester chloride were obtained in this manner in the form of a colorless oil with a boiling point of 146°–150° C./11 mm Hg.

2nd stage:

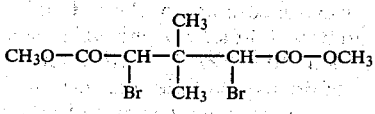

A mixture of 62.5 g (about 0.18 mol) of the ester chloride described above and 150 ml of methanol was stirred at room temperature for 2 hours, poured onto 500 ml of water and extracted 3 times with 100 ml of toluene each time. The organic phase was washed first with 50 ml of saturated sodium bicarbonate solution and then with 50 ml of water, dried over sodium sulphate and evaporated in vacuo. The residue was distilled in vacuo. 58 g (92% of theory) of 1,3-dibromo-2,2-dimethyl-propane-1,3-dicarboxylic acid dimethyl ester were obtained in this manner in the form of a slightly pink-colored oil with a boiling point of 105°–110° C./0.3 mm Hg.

Example 3

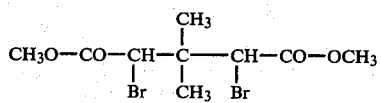

87 g (0.5 mol) of β,β-dimethyl-glutaric acid monomethyl ester (for the preparation, see S. F. Birch et al., J. Chem. Soc. (London) 1952, 1364) were added dropwise to 150 ml of thionyl chloride and the mixture was then boiled under reflux for 1 hour. 170 g of bromine were then added dropwise in the course of about 3 hours, while boiling the mixture further, and, after the addition had ended, the mixture was subsequently boiled for a further 1 hour. The reaction mixture was freed from excess thionyl chloride at about 50° C. in vacuo and then added dropwise to 250 ml of methanol, whereupon the temperature rose to the boiling point of methanol. The mixture was subsequently stirred for 1 hour and the solvent was then distilled off in vacuo. The residue was dissolved in 400 ml of toluene and the toluene solution was washed once with sodium bicarbonate solution and twice with water. The organic phase was dried over sodium sulphate and concentrated in vacuo. The residue was distilled under a high vacuum. 138 g (80% of theory) of 1,3-dibromo-2,2-dimethyl-propane-1,3-dicarboxylic acid dimethyl ester were thus obtained as a colorless oil with a boiling point of 98°–99° C./0.1 mm Hg.

Example 4

1st stage:

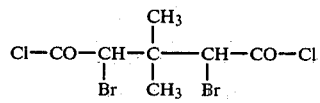

A mixture of 90 ml of thionyl chloride and 48.1 g (0.3 mol) of β,β-dimethyl-glutaric acid was boiled under reflux for half an hour, 68.8 g (0.33 mol) of phosphorus pentachloride were then added in portions at 50°–60° C. and 100.8 (0.63 mol) of bromine were subsequently added at 90°–100° C. The reaction mixture was subsequently stirred at 100° C. for 18 hours and fractionated in vacuo. 65 g (62% of theory) of 1,3-dibromo-2,2-dimethyl-propane-1,3-dicarboxylic acid dichloride with a boiling point of 128°–132° C./7 mm Hg were obtained in this manner.

2nd stage:

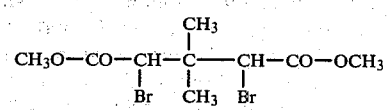

A solution of 17.8 g (0.05 mol) of 1,3-dibromo-2,2-dimethyl-propane-1,3-dicarboxylic acid dichloride in 50 ml of methanol was stirred for 2 hours and then evaporated in vacuo. The residue was dissolved in 100 ml of ether and the solution was shaken first with 50 ml of water, then with 50 ml of saturated sodium bicarbonate solution and finally twice more with 50 ml of water each time. After drying over sodium sulphate, the solvent was stripped off in vacuo and the residue was distilled. 14.2 g (83% of theory) of 1,3-dibromo-2,2-dimethyl-propane-1,3-dicarboxylic acid dimethyl ester with a boiling point of 100°–103° C./0.4 mm Hg were thus obtained.

Example 5

48.1 g (0.3 mol) of dimethyl-glutaric acid were added incrementally to 131 g (0.63 mol) of phosphorus pentachloride such that the temperature did not rise above 50° C. 100.8 g (0.62 mol) of bromine were added to the resulting mixture at 100° C. in the course of 3 hours and the mixture was subsequently stirred at 100° C. for 20 hours. After distilling off the volatile constituents, the product was added dropwise to 150 ml of methanol and the mixture was subsequently stirred for 1 hour. 300 ml of water were added to the reaction mixture and the mixture was extracted by shaking twice with 250 ml of toluene each time. The organic phases were washed first with 100 ml of saturated sodium bicarbonate solution and then twice with 100 ml of water each time, dried over sodium sulphate and evaporated in vacuo. The residue was distilled in vacuo. 83 g (80% of theory) of 1,3-dibromo-2,2-dimethyl-propane-1,3-dicarboxylic acid dimethyl ester with a boiling point of 138°–142° C./2 mm Hg were thus obtained.

It will be appreciated that the instant specification and examples are set forth by way of illustration and not limitation, and that various modifications and changes may be made without departing from the spirit and scope of the present invention.

We claim:
1. In the preparation of a 1,3-dibromo-2,2-dimethyl-propane-1,3-dicarboxylic acid derivative of the formula

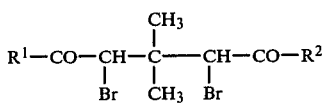

in which $R^1$ and $R^2$ each independently is chlorine or alkoxy, by reacting a 2,2-dimethyl-propane-1,3-dicarboxylic acid derivative of the formula

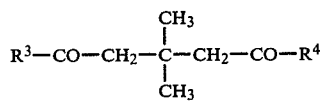

in which
$R^3$ is hydroxy or alkoxy and
$R^4$ is hydroxy,
with an acid halide, then reacting the product with bromine at a temperature between 0° and 150° C. to form a 1,3-dibromo-2,2-dimethyl-propane-1,3-dicarboxylic acid chloride and optionally reacting such acid chloride with an alkanol, the improvement which comprises employing as the acid halide phosphorus oxychloride, phosphorus trichloride, thionyl chloride or phosgene.

2. A process according to claim 1, in which
$R^3$ is hydroxy or $C_1$-$C_4$ alkoxy, and
$R^4$ is hydroxy 3. A process according to claim 1, in which the 2,2-dimethyl-propane-1,3-dicarboxylic acid derivative is 2,2-dimethyl-propane-1,3-dicarboxylic acid, or 2,2-dimethyl-propane-1,3-dicarboxylic acid monomethyl ester, monoethyl ester, mono-n-propyl ester, mono-isopropyl ester, mono-n-butyl ester, mono-iso-butyl ester, mono-sec.-butyl ester or mono-tert.-butyl ester.

4. A process according to claim 1, in which a mixture of acid chlorides is employed.

5. A process according to claim 1, in which the reaction of the 2,2-dimethyl-propane-1,3-dicarboxylic acid derivative is effected in the presence, as a catalyst, of a tertiary or heterocyclic amine, an ammonium salt, a carboxylic acid amide or a phosphorus compound.

6. A process according to claim 5, in which the catalyst is triethylamine, N,N-dimethyl-aniline, pyridine, tetraethylammonium chloride, dimethylformamide, dimethylacetamide, N-methyl-pyrrolidone, triphenylphosphine, triphenylphosphine oxide or hexamethylphosphoric acid triamide.

7. A process according to claim 1, in which 2,2-dimethyl-propane-1,3-dicarboxylic acid mono-ester is reacted at about 40° to 90° C. with about 1.2 to 3 mol equivalents of thionyl chloride, and subsequently about 1.9 to 2.2 mols of bromine, per mol of monoester, are added to the reaction mixture at about 70° to 90° C.

8. A process according to claim 1 in which the acid dichloride or chloride ester is esterified in situ by reaction with an alkanol at about 10° to 80° C. after distilling off the halogenating agent.